United States Patent [19]

Knapp, Jr. et al.

[11] Patent Number: 4,683,123
[45] Date of Patent: Jul. 28, 1987

[54] OSMIUM-191/IRIDIUM-191M RADIONUCLIDE

[75] Inventors: Furn F. Knapp, Jr.; Thomas A. Butler, both of Oak Ridge, Tenn.; Claude Brihaye, Liege, Belgium

[73] Assignee: The United States of America as represented by the United States Department of Energy, Washington, D.C.

[21] Appl. No.: 769,519

[22] Filed: Aug. 26, 1985

[51] Int. Cl.$^4$ ............................................. B01D 59/26
[52] U.S. Cl. .................................. 423/2; 250/432 PD; 252/645; 423/22
[58] Field of Search .............. 423/2, 22; 250/432 PD; 252/645; 424/1.1

[56] References Cited

U.S. PATENT DOCUMENTS 3,848,048  11/1974  Moore ..................................... 423/2

FOREIGN PATENT DOCUMENTS 2161979  1/1986  United Kingdom .................... 423/2

OTHER PUBLICATIONS

Panek, K., et al., Radionuclide Generators–New Systems for Nuclear Medicine Applications, Am. Chem. Soc. Advances in Chemistry, Series No. 241 (F. Knapp, Jr. and T. Butler, Eds.) pp. 3-21, 1984.
Packard, A. B., et al., Radionuclide Generators: New Systems for Nuclear Medicine Applications, (ACS Symp. Ser. 241), p. 51, 1983.
Mughabghab, S. et al., Neutron Cross Sections, vol. 1, Brookhaven Nat'l Lab. 325, 3rd ed., 1973.
Panek et al, "A New Generator for Production of Short-Lived Au-195m Radioisotope, pp. 3-21.
Campbell et al, "Rapid Ion-Exchange Techniques for Radiochemical Separations," J. Inorg. Nucl. Chem., pp. 233-242.
Yano et al, "Ultrashort-Lived Radioisotopes for Visualizing Blood Vessels and Organs," Journal of Nuclear Medicine, pp. 2-6.
Cheng et al, "Iridium-191 Angiocardiography for the Detection and Quantitation of Left-to--Right Shunting," The Journal of Nuclear Medicine, pp. 1151-1157.
Packard et al, "Chemical and Physical Parameters Affecting the Performance of the Os-191/Ir-191m Generator," pp. 51-66.

Primary Examiner—John F. Terapane
Assistant Examiner—Virginia B. Caress
Attorney, Agent, or Firm—Katherine P. Lovingood; Stephen D. Hamel; Judson R. Hightower

[57] ABSTRACT

A generator system to provide iridium-191m for clinical imaging applications comprises an activated carbon adsorbent loaded with a compound containing the parent nuclide, osmium-191. The generator, which has a shelf-life in excess of two weeks and does not require a scavenger column, can be eluted with physiologically compatible saline.

25 Claims, 4 Drawing Figures

OSMIUM-191/IRIDIUM-191M RADIONUCLIDE

BACKGROUND OF THE INVENTION

The present invention, which resulted from a contract with the U.S. Department of Energy, to an improved osmium-191 ($^{191}$Os)/iridium-191m ($^{191m}$Ir) radionuclide generator which is based on an activated carbon adsorbent. The generator can be used to obtain rapid-sequence venograms and angiograms from different angles and locations relative to the injection site of the radioisotope.

Ultra-short-lived radionuclides, i.e., those having physical half-lives ranging from seconds to several minutes, can be injected intravenously either by a small rapid injection or by continuous infusion. With such nuclides, dynamic radiotracer studies can be performed repeatedly in patients within a very short time. They also provide high photon flux for imaging while dilivering low radiation dose to the patient.

Iridium-191m, with a physical half-life of 4.96 sec, can be used for radionuclide angiography. Decaying by isomeric transition to stable Ir-191, Ir-191m emits x-rays, at about 65 KeV and a 129-keV gamma photon; these are in 58% and 30% abundance, respectively. Both photons can be imaged with modern gamma scintillation cameras. Because of the short physical half-life of Ir-191m, relatively large amounts of activity can be administered to the patient with much lower radiation exposure than with relatively smaller doses of Tc-99m. The high photon flux available with Ir-191m permits rapid imaging with high information density. With Ir-191m, serial studies in the same patient only a few seconds apart can be carried out without interfering background from previous administrations. In this way, the heart and great vessels can be evaluated in a variety of conditions.

Iridium-191m is the product of decay of osmium-191, which has a physical half-life of 15.4 days. The half-life of Os-191 is sufficiently long to accommodate transportation, generator construction, quality control, and clinical use. In addition, Os-191 can be produced relatively inexpensively. Accordingly, the Os-191→Ir-191m system, wherein the short-lived daughter isotope is separated from the long-lived parent by elution from a generator or "cow," provides several recognized advantages over other generators studied for clinical application, such as the rubidium-81→krypton-81m system. See Panek et al in RADIONUCLIDE GENERATORS—NEW SYSTEMS FOR NUCLEAR MEDICINE APPLICATIONS (Am. Chem. Soc. Advances in Chemistry, Series No. 241) 3–21 (F. F. Knapp, Jr. & T. A. Butler eds. 1984), the contents of which are incorporated by reference.

Ion exchange techniques have been used to effect Os-191/Ir-191m separation. Campbell & Nelson, 3 J. INORG. NUCL. CHEM. 233 (1956). An osmium-191→iridium-191m generator designed for medical purposes has been described which employs a Bio-Rad 1×8 cm anion-exchange resin column as an adsorbent for Os-191 hexachloroosmate [osmium(IV)]. Yano & Anger, 9 J. NUCL. MED. 2 (1968). More recently, a generator incorporating another Bio-Rad resin, AGMP-1, has been reported. Cheng et al, 21 J. NUCL. MED. 1151 (1980). In both of these generator types, a second "scavenger" column in series with the resin exchange column is needed to adsorb excessive "breakthrough" of the parent Os-191 isotope into the eluant. Accordingly, the useful life of both generators is adversely affected by elution of the parent isotope from the adsorbent, resulting in a high radiation dose to the patient.

SUMMARY OF THE INVENTION

It is therefore an object of the present invention to provide an osmium-191/iridium-191m generator characterized by good yield of Ir-191m and consistently low breakthrough of Os-191.

It is another object of the present invention to provide a radionuclide generator which does not require a second scavenger column to adsorb eluted parent isotope, and which has an extended service life well-suited to clinical applications.

It is yet another object of the present invention to provide a method for providing Ir-191m for clinical use by means of the above-mentioned osmium-191/iridium-191m generator.

In accomplishing the foregoing objects, there has been provided, in accordance with one aspect of the present invention, an osmium-191/iridium-191m generator comprising an adsorbent comprised of activated carbon, the adsorbent being loaded with a compound containing Os-191. In one embodiment of the present invention, the adsorbent-loaded compound is potassium hexachloroosmate(IV). In another embodiment, the activated carbon of the generator is susbstantially free of KI and $I_2$.

In accordance with another embodiment of the present invention, there has been provided a method for providing Ir-191m for clinical use, comprising the steps of (a) loading an adsorbent comprised of activated carbon with a compound containing Os-191 and then (b) contacting the adsorbent with a predetermined volume of a physiologically compatible saline solution, whereby Ir-191m is eluted from the adsorbent in the volume of solution. In a preferred embodiment, the aforesaid saline solution comprises KI.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENT

In this description, "activated carbon" denotes an adsorbent which is the product of activating, either thermally or by chemical means, any highly carbonaceous raw material, such as sawdust, lignite, bituminous coal or coconut shells. The adsorbent used in the present invention can be comprised of any of a number of commercially available carbon products, e.g., those shown in Table 1, or a mixture thereof.

TABLE 1

CARBON PRODUCTS SUITABLE AS ADSORBENT MATERIAL

| Manufacturer/Product | Characterization |
|---|---|
| ICI Americas (Marshall, TX): | |
| DARCO ® 4 × 12 | Lignite carbon |
| DARCO ® LI-100 | Coal carbon (low iron) |
| DARCO ® H-85 | Coal-based carbon (85 hardness) |
| DARCO ® 20 × 40 | Lignite carbon |
| DARCO ® 12 × 20 LI | Lignite carbon (low iron) |
| Fischer (Norcross, GA) | Coconut shell |
| Barneby-Cheney (Columbus, OH) | Coconut shell |

Barneby-Cheney (coconut shell) carbon is preferred as adsorbent material.

The carbon product of choice should be pulverized to a particle size which maximizes adsorbent surface area (for good Os-191 binding and Ir-191m release, respectively) and permits rapid elution (approximately 1 second or less elution time) under the system pressure utilized. (As described in greater detail below, the generator system of the present invention can also be used to obtain a slower, continuous elution, in order to maintain a constant level of radioactivity in the region of interest.) Activated carbon particles in the size range of 140–230 mesh, relative to U.S. standard sieves (manufactured by Becton, Dickinson & Co., Rutherford, NJ), have been used to advantage.

It has also proven advantageous to heat-treat the activated carbon prior to fabricating the generator of the present invention. More specifically, chemical analyses of commercial carbon products revealed the presence of KI and $I_2$ in varying amounts. Removal of most or all of the KI and $I_2$ from the carbonaceous starting material, e.g., by heating the carbon particles at an elevated temperature (about 800°–900° C.) for some 4 to 6 hours in a chemically inert atmosphere, e.g., a stream of argon, resulted in unexpectedly more consistent, higher Ir-191m yield and less Os-191 breakthrough.

Figure 3:
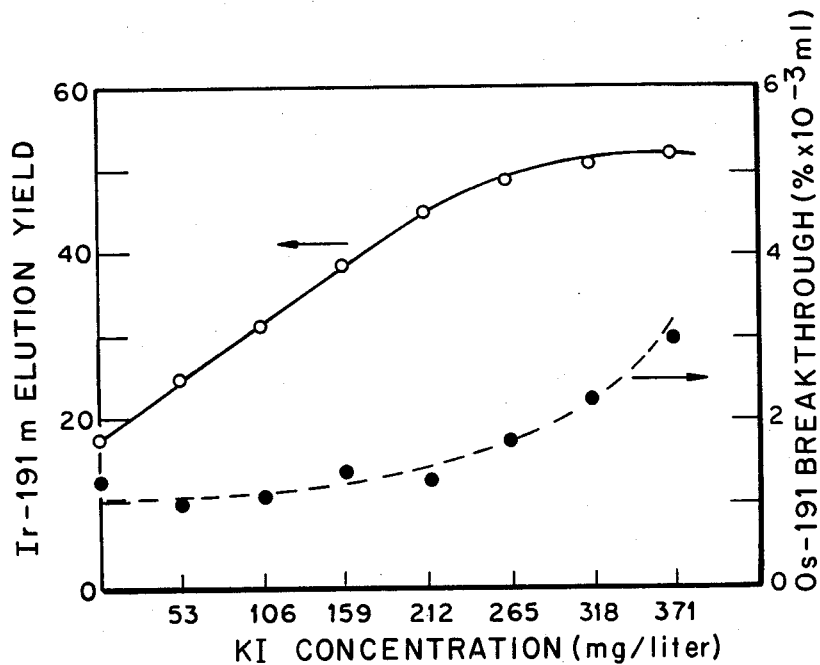
FIG. 3 is a graph showing, respectively, Ir-191m elution and Os-191 breakthrough in a generator of the present invention, as a function of KI concentration in the eluting solution.

In contrast, use in the present invention of commercially available activated carbon which had not been heat-treated in the aforesaid manner resulted in reasonable yield of the daughter radionuclide, as well as acceptable breakthrough initially. But the amount of breakthrough increased rapidly with the volume of saline eluted from the generator, adversely affecting the useful life of the generator. (See FIG. 3, where the solid line tracks Ir-191m yield and the broken line Os-191 breakthrough.) Accordingly, activated carbon which is substantially free of KI and $I_2$ is preferred.

Figure 1:
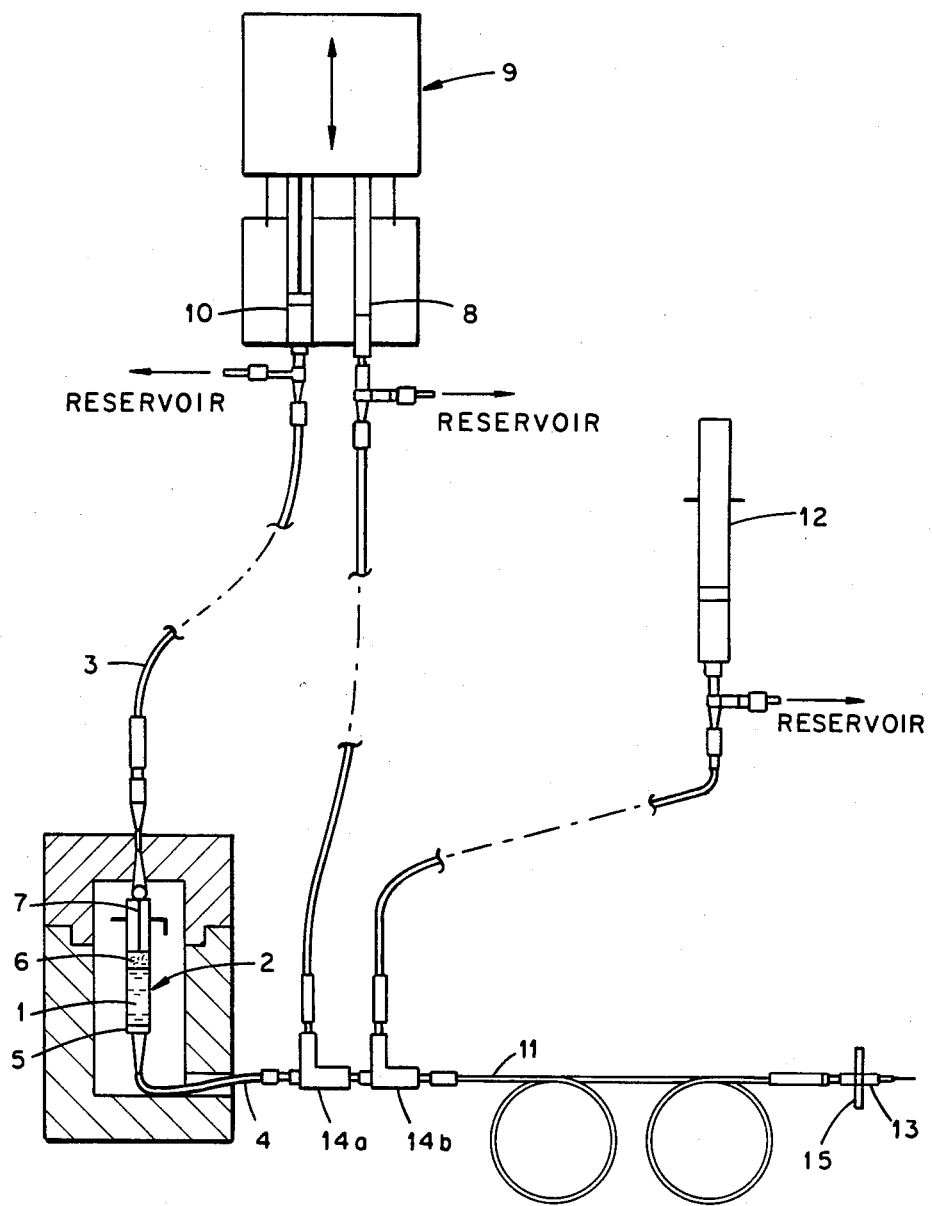
FIG. 1 is a schematic diagram of a radionuclide generator system within the present invention.

In FIG. 1, an exemplary system of the present invention for generating Ir-191m for clinical use is depicted. The activated carbon adsorbent 1, which is preferably in the form of a slurry of particulate carbon in distilled water, is contained in a syringe cannula 2 (approximately 1–2 ml volume) fitted with a feed line 3 and output conduit 4.

After the activated carbon adsorbent has been introduced into a syringe cannula or other suitable container, the adsorbent can be loaded with a compound that contains Os-191. Osmium-191 is produced by neutron irradiation of isotopically enriched Os-190 (isotopic composition: Os-190, 97.8%; Os-188, 0.47%; Os-192, 1.02%), as described by Packard et al in RADIONUCLIDE GENERATORS: NEW SYSTEMS FOR NUCLEAR MEDICINE APPLICATIONS p. 51 (ACS Symp. Series 241) (F. F. Knapp, Jr. & T. A. Butler eds. 1983), the contents of which are incorporated herein by reference. Osmium-191 can be obtained from the Oak Ridge National Laboratory (Oak Ridge, TN), where irradiation is performed in the High Flux Isotope Reactor at a neutron flux of $2.5 \times 10^{15}$ n/cm$^2$-s. The routes to the various nuclides produced during irradiation of an Os-190 target and the neutron cross-section values, obtained from S. F. MUGHABGHAB and D. I. GARBER, vol. 1, NEUTRON CROSS SECTIONS (BNL 325) (3d ed. 1973), are summarized below (Scheme I):

Scheme I.
Production scheme for Os-191.

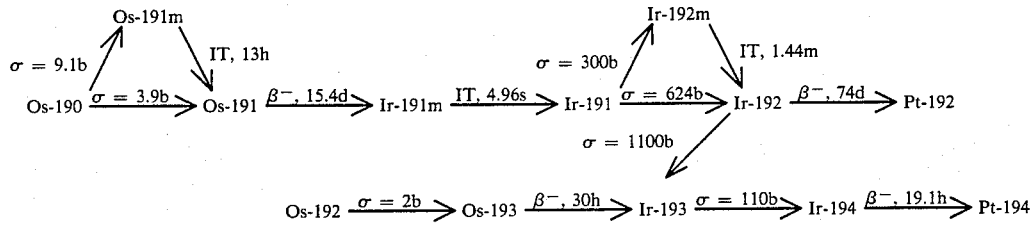

After irradition, the Os-191 is added to a solid KOH—KNO$_3$ mixture, and the mixture is then heated at a temperature sufficiently high to fuse the mixture. The resultant solid material is thereafter dissolved in water to produce an aqueous solution of potassium per (Os$^{191}$) osmate(IV) (see FIG. 1), which can be used, as described in greater detail below, to derive Os$^{191}$-containing compounds suitable for loading the generator of the present invention. Generally, compounds representative of osmium oxidation states (VI), (IV) and (III) are preferred because they are easy to prepare and are relatively stable in aqueous media. Since osmium oxidation state (IV) is widely considered the most stable, compounds representative of the (IV) state are particularly preferred.

In the Ir-191m generator system shown in FIG. 1, a plug 5, comprised of glass wool or other similar material, is placed in the bottom of the 1 cc syringe (2) to retain the activated carbon (approximately 0.87 cc) introduced as a slurry into the column. Optionally, the bottom of the syringe can be fitted with a Millipore-Millex filter (0.22 μm) having a standard luer taper. At the top of the column, a fine layer of glass wool (6) or similar material is provided to cover the activated carbon bed, and a plunger 7 (preferably polytetrafluoroethylene) is snugly inserted into the syringe barrel. Plunger 7 is provided with a bore hole (inner diameter of about 1 mm) along its longitudinal axis which can be fitted with tubing connectors to permit ready introduction of samples into the column.

The activated carbon adsorbent of an Ir-191 generator within the present invention is preferably eluted with a physiological saline solution, such a 0.9% NaCl-0.1M HCl solution, having a pH between 0 and about 5. It is particularly preferred that the eluant contain an alkali iodide, such as potassium iodide at a concentration between about 0.1 and 0.5 g/l. Why inclusion of an alkali iodide in the eluting solution is beneficial is unclear, particularly since the adsorbent itself preferably does not contain KI and $I_2$. Nevertheless, it has been determined empirically that the presence of an alkali iodide in the eluent results in improved yield and decreased breakthrough for a generator within the present invention.

Because the aforesaid saline solution is acidified, it should be neutralized after elution, e.g., with a Tris buffer, to give an isotonic solution that has a physiological pH and is ready for direct intravenous injection.

With reference to FIG. 1, neutralization of the acidic eluate is accomplished by means of a second syringe 8 containing Tris buffer acidified with HCl. Upon activation of syringe pump 9, syringe 8 is emptied simultaneously with syringe 10, which contains the eluting solution, resulting in immediate neutralization of the column eluate at three-way connector 14a. The eluted bolus is stored in a 3-ml extension tube 11, to be injected into the patient as quickly as possible, via an injection syringe 13, with physiological solution which is contained in syringe 12 and is introduced into the system through three-way connector 14b. Injection syringe 13 can be fitted with a Millipore filter (15).

In the system illustrated in FIG. 1, commercial two-way connectors (XKEM-001-04; marketed by Millipore, Inc., Bedford, MA) are used along with readily available intravenous extension tubing and arterial pressure tubing. For shielding, standard 2-inch lead shipping pigs are modified as shown so that the pig can be used as the shielded container for the column. In this way, the shipping pip can be used for shielding after receipt by the ultimate use, eliminating the need to transfer the generator column to a second shielded container. The extension tubing can simply be attached to the short lengths of tubing which are capped with luer dead-end caps during shipment. If desired, the generator system of the present invention can be readily automated, e.g., by employing a microprocessor to control elution and, thereby, accurately and reproducibly elute any elution volume.

The present invention is further described by the following illustrative examples.

EXAMPLE 1

Preparation of Os-191 solutions for loading of generator

Exemplary osmium-191 compounds suitable for use in the present invention are potassium tetrachloroosmate(VI), $K_2[OsO_2Cl_4]$; potassium hexachloroosmate(IV), $K_2OsCl_6$; and potassium hexathiocyanatoosmate(III), $K_3[Os(SCN)_6]$. In HCl solution, these compounds are stable for at least 2 days, which is a sufficient period for preparation of the Ir-191m generator of the present invention.

The starting material for the preparation of the abovementioned compounds is potassium perosmate(VIII), $K_2[OsO_4(OH)_2]$, prepared, as mentioned previously, by neutron irradiation of isotopically enriched (97.8%) granulated metallic osmium in the Oak Ridge National Laboratory High Flux Isotope Reactor, with subsequent fusion in a mixture of KOH—$KNO_3$ and dissolution in water, following the procedure of Cheng et al, J. NUCL. MED. 21: 1169 (1980), the contents of which are incorporated herein by reference.

The determination of the osmium(VIII) content in solution was performed via a modification of the method described by Ryabchikov, EH. PRIKIL, KHIM. 17: 326 (1944) [summarized in CHEM. ABSTR. Vol. 39, abstract no. 29416 (1945)]. A 0.5 ml aliquot of the perosmate solution, corresponding to about 3.5 mg of osmium, wad added to 30 ml of 1N $H_2SO_4$. After addition of 1.0 g of KI, the solution was left for 1 hour at which time the reaction was complete. The iodine formed was titrated with 0.01N $Na_2S_2O_3$, and the end point detected potentiometrically with platinum and calomel electrodes.

Figure 2:
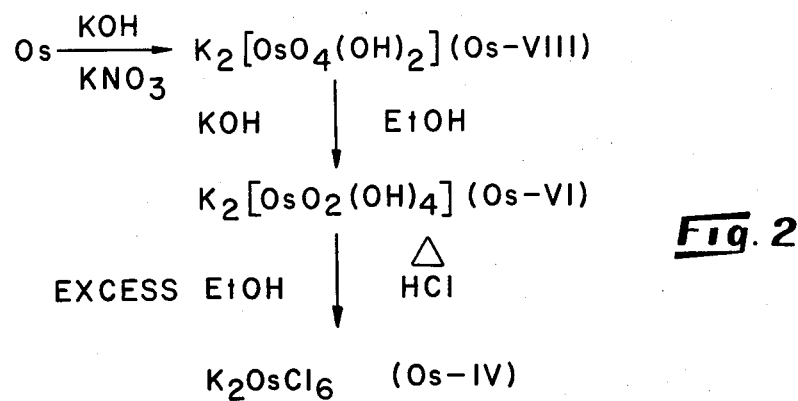
FIG. 2 shows a reaction sequence for the preparation of an osmium (IV)-containing compound suitable for use in loading a generator of the present invention.

Potassium osmate(VI), $K_2[OsO_2Cl_4]$, was prepared by reduction of potassium perosmate(VIII) with ethanol in basic solution, following the procedure shown diagrammatically in FIG. 2. A portion of the persomate solution, which was about 0.4N KOH, was mixed with 9 parts of 95% ethanol. After about 15 minutes, the purple precipitate of $K_2[OsO_2(OH)_4]$ was centrifuged and the solution decanted. The precipitate was washed twice with 5 ml of 95% ethanol, air dried, dissolved in 0.5 ml of 4N HCl, and the resulting solution was diluted to 2 ml with water. Determination of osmium(VI) in this solution was performed by potentiometric titration with a 0.01N $KMnO_4$ solution in 0.6N KOH, as described by Santrucek et al, MICROCHIM. ACTA 1966: 10, and it was found that the reduction to the oxidation state (VI) was completed, no loss having occurred during the process.

Potassium hexachloroosmate(IV) was prepared by refluxing a solution of Os(VIII) for 4 hours in concentrated hydrochloric acid in the presence of alcohol, following the method of Turner et al, ANAL. CHEM. 30: 1709 (1958). It had been determined beforehand, by means of a solution of potassium [$^{191}Os$] persomate, that significant loss of activity (10–20%) occurred due to the high volatility of osmium tetroxide. To avoid this inconvenience, an alternative two-step procedure was developed. Two volumes of ethanol were added to one volume of basic potassium perosmate solution to reduce the osmium(VIII) to osmium(VI), thus avoiding Os(VIII) volatility problems. After 10 minutes, five volumes of concentrated hydrochloric acid were added quickly, and the solution was heated in a boiling water-bath for 30 minutes. The solution was then evaporated to dryness, and the brick-red precipitate of $K_2OsCl_6$ dissolved in 0.9% NaCl-0.01N HCl. The kinetics of the reduction of potassium tetrachloroosmate(VI) in concentrated HCl in the presence of alcohol were followed spectrometrically. The 370 nm absorbance corresponding to the maximum of a peak characteristic of $K_2OsCl_6$, see, e.g., Miano & Garner, INORG. CHEM. 4: 337 (1965), reached a maximal value after 15 minutes of heating and was constant up to 5 hours of heating. The use of an Os-191 solution of perosmate showed that the yield of conversion to $K_2OsCl_6$ was 100%. No loss was detected during the evaporation step.

Osmium(IV) content was determined by oxidizing osmium(IV) to osmium(VI) with a known volume of 0.01N NH4VO3 in 6N H2SO4 and thereafter titrating potentiometrically the excess of ammonium metavanadate with a 0.01N ferrous sulfate solution, in accordance with Syrokomskii, DOKLADY AKAD. NAUK. SSSR 46: 307 (1945) [summarized in CHEM. ABSTR. Vol. 39, abstract no. 51999 (1945)]. By this approach, it was confirmed that the reduction was complete and quantitative.

Potassium hexathiocyanoosmate(III) was prepared by adding ten equivalents of KSCN to a solution of $K_2OsCl_6$ in 0.01N HNO3, which was then heated at 80° C. for 24 hours, following the method disclosed by Peters and Preetz, NATURFORSCH. 356: 994 (1980). A higher temperature was avoided since it would have induced the formation of secondary reaction products (black precipitate). The end product was characterized as the desired hexathiocyanaoosmate by comparing the melting point and IR spectrum of its tertbutylammonium salt with published data. See Schmidtke & Garthoff, HELV. CHIM. ACTA. 50: 1631 (1967).

EXAMPLE 2

Comparison of Elution Characteristics of Various Activated Carbons

Several commercially available activated carbons were pulverized in a mortar and pestle and sieved through U.S. standard sieves (W. S. Tyler Co., Cleveland, OH). The 140–230 mesh fraction for each carbon was used, respectively, to prepare a column, which possessed sufficient surface area for good Os-191 binding and Ir-191m release but did not need an elution pressure that interfered with rapid ($\leq 1$ second) elution. The 140–230 mesh fraction derived from Barneby-Cheney (Type PC) activated carbon was heated for 4–6 hours at 800°–900° C. under a stream of argon, thereby effectively removing large amounts of KI and $I_2$ and destroying the oxygen surface functional groups contained in the fraction.

The carbon fractions were separately slurried in distilled water and loaded into 1 ml syringes plugged with glass wool. Ten mCi of a solution of $K_2OsCl_6$ prepared as described above were loaded by a pump onto each column at a flow-rate of 1 ml/h. The columns were then washed with 20 ml of 0.9% NaCl solution (pH 2) at 3 ml/h. Samples of the fixation and wash solutions were counted to determine Os-191 fixation and Ir-192 elution percentage. The columns were washed manually with 50 ml of 0.9% NaCl (pH 2), and yield and breakthrough were then measured using a 5 ml bolus (see Table 2).

TABLE 2

SUMMARY OF THE PROPERTIES OF DIFFERENT SOURCES OF CARBON AS ADSORBENTS FOR AN OSMIUM-191/IRIDIUM-191 m GENERATOR SYSTEM WITHIN THE PRESENT INVENTION

| Activated Carbon | Osmium Fixation (%) | Iridium-192 Eluted (%) During Fixation | Iridium-191 m[a] Yield (%) | Osmium-191 Breakthrough (%/5 ml) |
|---|---|---|---|---|
| DARCO ® | | | | |
| 4 × 12 | 99.6 | 36.4 | 32.4 | $9.3 \times 10^{-3}$ |
| LI-100 | 99.9 | 11.5 | 4.5 | $4.9 \times 10^{-3}$ |
| H-85 | 99.8 | 11.7 | 4.2 | $1.3 \times 10^{-2}$ |
| 20 × 40 | 99.9 | 6.5 | 18.8 | $3.7 \times 10^{-3}$ |
| 12 × 20 LI | 99.8 | 7.1 | 23.6 | $6.7 \times 10^{-3}$ |
| Fischer | 99.9 | 10.3 | 18.8 | $6.2 \times 10^{-3}$ |
| Barneby-Cheney | 99.9 | 31.5 | 31.4 | $2.8 \times 10^{-3}$ |

[a]Each bolus consisted of a 5 ml volume.

Because of the very short (4.96 second) half-life of Ir-191m, special techniques described by Cheng et al, supra, were used for determination of Ir-191m yield. After elution of the generators, the Ir-191m was allowed to decay for a sufficient time to overcome large gross count loss resulting from the detector deadtime. The decay period, denoted as the waiting time, $T_W$, was monitored accurately. (A digital timer proved very convenient for this purpose, since $T_W$ could be varied depending upon the levels of Ir-191m eluted.) After a waiting time of $T_W$ seconds, the eluate was counted with a NaI(Tl) detector connected to a multichannel analyzer under standardized geometric conditions. Samples were counted for $T_C$ seconds, where $T_C$ corresponds to at least eight times the half-life of the daughter nuclide (i.e., at least 40 seconds). The energy and the intensity of the measured gamma-ray were 129.4 keV and 0.259, respectively.

After the decay of the Ir-191m, the samples were counted again for $T_C$ seconds to determine the contribution of the Os-191 to the number of counts previously measured (breakthrough). The levels of Ir-192 eluted in the bolus were also determined.

The Ir-191m activity, A (Ir-191m), in microcuries at the end of the bolus elution was calculated by the relationship:

$$A\ (\text{Ir-191}m) = \frac{[N(\text{Ir-191}m) - N(\text{Os-191})]x}{\epsilon \times \gamma \times 3.7 \times 10^4 \times e^{-\lambda T_W}} \quad (1)$$

where

A (Ir-191m) = Ir-191m activity in the sample at the end of elution (μCi),

N (Ir-191m) = gross number of counts of Ir-191m measure for $T_C$ seconds,

N (Os-191) = net number of counts measured for $T_C$ seconds for Os-191 after decay of eluted Ir-191m, $\lambda$ = decay constant of Ir-191m (s$^{-1}$), $\epsilon$ = efficiency of the counter at the energy of measurement under the prevailing geometrical conditions, $\gamma$ = intensity of the gamma-ray measured, and $T_W$ = waiting time before counting (seconds).

The elution yield, Y(%), was obtained by the relationship:

$$Y(\%) = \frac{A\ (\text{Ir-191}m) \times 100}{A\ (\text{Os-191})} \quad (2)$$

where A (Os-191) is the Os-191 activity in μCi on the column. The contribution of Os-191 to activity in the samples was determined as described above, and the Os-191 breakthrough was calculated as the ratio of the Os-191 activity in the eluate solution to the Os-191 activity on the column. The values for Os-191 breakthrough measured in this manner are the "worst case" figures, and thus must be considered with reserve, since the Os-191 activity was spread throughout any given column and, consequently, no free exchanger was available to reduce the Os-191 breakthrough.

EXAMPLE 3

Preparation and Loading an Ir-191m Generator within the Present Invention

A 140-230 mesh, heat-treated Barneby-Cheney carbon fraction, prepared in the manner described in Example 2, was slurried in distilled water and washed successively by contrifugation until the decanted solution was clear. The resulting carbon slurry was added to a syringe cannula (2 ml) of a generator system as described above with reference to FIG. 2.

Prior to loading, the column was washed with 20 ml of 0.9% NaCl (pH 2) prepared by adding 20 ml of 0.5M HCl to 980 ml of physiological saline solution. The generator of the present invention was then loaded with the above-described Os-191(IV) solution, via a syringe pump, at a rate of about 0.25 ml/min and washed with 20 ml of 0.9% NaCl solution (pH 2) at the same flow rate. The system was then washed with 50 ml of 0.9% NaCl eluting solution (pH 2) containing 0.250 gm KI/liter (0.025%). Thus prepared, the generator system of the present invention was ready for use, and had a shelf-life of more than two weeks.

Figure 4:
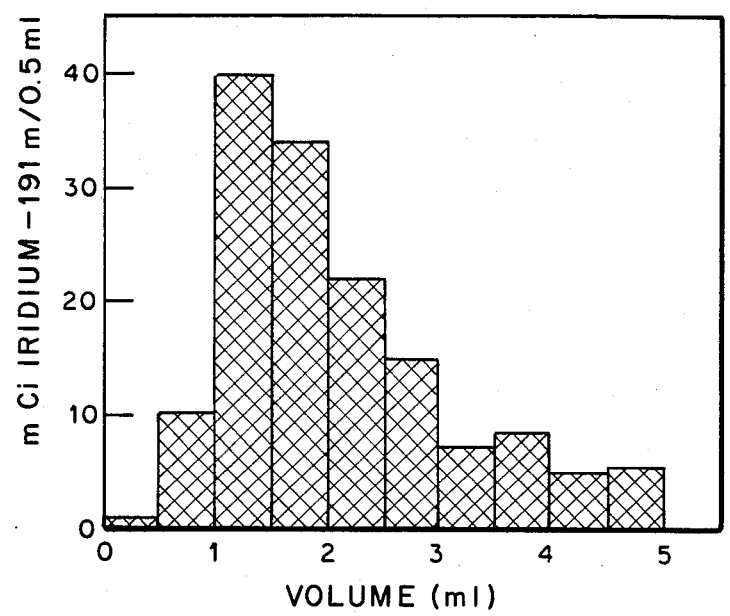
FIG. 4 is a graph showing a typical Ir-191m elution profile of a generator within the present invention.

As is typical for a generator system within the present invention, the above-described generator was loaded with 700 mCi of Os-191(IV) (specific activity=200 mCi/mg), and the Ir-191m bolus eluted with 2.5 ml of the eluting solution. A typical elution profile is shown in FIG. 4. With a 2.5 ml volume, 85% of the equilibrium bolus activity was eluted with the activity effectively contained in 2.0 ml, since the activity in the first 0.5 ml could be neglected. The elution characteristics of the above-described generator are summarized in Table 3 below. The Ir-191m elution yield and the Os-191 breakthrough, calculated as in Example 2, were independent of time, and a volume of 1000 ml could be passed through the generator without altering its properties. The acid eluate was neutralized, as described above, by the addition thereto of 0.4 ml of 0.13M Tris buffer acidified to pH 8.4 with HCl.

The generator can also be eluted continuously. The measure the elution yield of a generator continuously eluted at a flow rate of f (ml/min), 1 ml is sampled after the passage of the equilibrium activity bolus for $T_S$ seconds ($T_S=60/f$) and counted in the same manner as for bolus. The Ir-191m activity then is calculated by relationship (1) above. The elution yield is then given by the following relationship:

$$Y(\%) = \frac{A\ (Ir\text{-}191m) \times 100}{A\ (Os\text{-}191) \times (1 - e^{-\lambda T_S})} \quad (3)$$

When the generator system shown in FIG. 1 was eluted continuously, a low mean elution yield of 3.7% was measured at a flow rate of 12 ml/min, with a mean Os-191 breakthrough as low as $2.0 \times 10^{-5}\%$/ml. Due to the short half-life of the daughter nuclide used in the present invention, the replacement of Ir-191m eluted from the equilibrium mixture of Os-191 and Ir-191m in the generator is quite rapid. Even for such a low elution yield, therefore, the elution rate of Ir-191m is as high as 1.3 mCi/sec at 12 ml/min for a 250 mCi Os-191 generator, making the injection of 6.5 mCi of Ir-191m per injected ml possible. This latter activity is sufficient for many medical applications requiring continuous infusion. The Ir-192 activity was measured to be 0.020 μCi/ml. A volume of 2 liters was passed through the generator before the Os-191 breakthrough increased to $5 \times 10^{-5}\%$/ml.

EXAMPLE 4

Clinical Application of the Ir-191 Generator System of the Present Invention

Preliminary gamma scintillation camera studies on human volunteers were performed in comparison with conventional technetium-99m imaging to demonstrate utility of the present invention in clinical applications, such as the measurement of cardiac functions, the evaluation of venous and arterial drainage, renal and cerebral perfusion, and the diagnosis of peripheral occlusions. For these applications, a typical injection of 70 mCi of Ir-191m from a generator of the present invention gives, in those regions of interest in the patient identified as peak areas for radionuclide concentration, a similar total number of counts as were obtained with 20 mCi of Tc-99m. Under these conditions, mean radiation dose estimates were 1.2 mRad ($^{191m}$Ir), 2.5 mRad ($^{191}$Os) and 7.3 mRad ($^{192}$Ir). No adverse effects have been detected on more than 40 volunteers.

The generator system of the present invention provides an easy, safe and widely applicable tool for func-

TABLE 3

ELUTION CHARACTERISTICS OF OSMIUM-191/IRIDIUM-191 m GENERATOR PREPARED FROM HEAT-TREATED 140-230 MESH BARNEBY-CHENEY CARBON LOADED WITH OS-191(IV)

| | | | Values per 2 ml Bolus | | |
|---|---|---|---|---|---|
| Bolus No. | Total[a] Volume (ml) Eluted | Elapse Time (days) | Iridium-191 m Yield (%) | Osmium-191 Breakthrough (%/2 ml) | Iridium-192 (μCi) |
| 1 | 50 | 0 | 18 | 2.9 10$^{-4}$ | 0.7 |
| 50 | 175 | 1 | 17 | 2.5 10$^{-4}$ | 0.5 |
| 80 | 250 | 3 | 19 | 2.3 10$^{-4}$ | 0.4 |
| 110 | 325 | 8 | 18 | 2.3 10$^{-4}$ | 0.3 |
| 150 | 475 | 15 | 19 | 1.6 10$^{-4}$ | 0.2 |
| 280 | 750 | 20 | 21 | 1.7 10$^{-4}$ | 0.2 |
| 380 | 1000 | 22 | 22 | 1.8 10$^{-4}$ | 0.3 |

[a] Each bolus consisted of a 2 ml volume eluted in approximately 1 sec.

tional hemodynamic imaging. Needing neither a scavenger column nor periodic reverse elutions, the generator system of the present invention can be used with either the bolus- or the continuous-injection technique.

What is claimed is:

1. An osmium-191/iridium-191m generator system comprising an adsorbent consisting essentially of activated carbon, said adsorbent being loaded with a compound containing Os-191.

2. A generator system according to claim 1, wherein said Os-191 comprises gamma-emitting osmium in oxidation state (IV).

3. A generator system according to claim 1, wherein said compound is selected from the group consisting of potassium tetrachloroosmate(VI), potassium hexachloroosmate(IV) and potassium hexathiocyanatoosmate(III).

4. A generator system according to claim 3, wherein said compound is potassium hexachloroosmate(IV).

5. A generator system according to claim 4, wherein said adsorbent is loaded by contact with a saline solution of potassium hexachloroosmate(IV).

6. A generator system according to claim 1, wherein said activated carbon is derived from a source selected from the group consisting of lignite, bituminous coal and coconut shell.

7. A generator system according to claim 6, wherein said activated carbon is heated for about 4 to 6 hours at between about 800° and 900° C. in a chemically inert atmosphere before being loaded with said compound.

8. A generator system according to claim 1, wherein said activated carbon comprises particles in the size range of 140–230 mesh.

9. A generator system according to claim 1, wherein said activated carbon is substantially free of KI and $I_2$.

10. A generator system according to claim 1, further comprising (i) a source of physiological saline eluant solution and (ii) means for delivering said eluant solution to said adsorbent.

11. A generator system according to claim 1, further comprising (i) container means for containing said adsorbent, (ii) injection means for injecting eluate from said adsorbent into a patient and (iii) means for connecting said container means directly to said injection means.

12. A method for providing Ir-191m for clinical use, comprising the steps of
 (a) loading an adsorbent consisting essentially of activated carbon with a compound containing Os-191,
 (b) contacting said adsorbent with a predetermined volume of a physiologically compatible saline solution, whereby Ir-191m is eluted from said adsorbent in said volume of solution.

13. A method according to claim 12, further comprising prior to step (a) the step of heating said adsorbent at between about 800° and 900° C. for about 4 to 6 hours in a chemically inert atmosphere.

14. A method according to claim 12, wherein said saline solution comprises an alkali iodide.

15. A method according to claim 14, wherein said alkali iodide is KI.

16. A method according to claim 12, wherein said saline solution has a pH between 0 and about 5.

17. A method according to claim 16, further comprising after step (b) adjusting said pH of said saline solution to physiological pH.

18. A method according to claim 16, wherein said saline solution is a 0.9% NaCl solution having a pH of about 2.

19. A method according to claim 12, wherein said activated carbon is substantially free of KI and $I_2$.

20. A method according to claim 12, wherein said Os-191 comprises gamma-emitting osmium in oxidation state (IV).

21. A method according to claim 12, wherein said compound is selected from the group consisting of potassium tetrachloroosmate(VI), potassium hexachloroosmate(IV) and potassium hexathiocyanatoosmate(III).

22. A method according to claim 21, wherein said compound is potassium hexachloroosmate(IV).

23. A method according to claim 12, wherein said activated carbon is derived from a source selected from the group consisting of lignite, bituminous coal and coconut shell.

24. A method according to claim 12, wherein said activated carbon comprises particles in the size range of 140–230 mesh.

25. A method according to claim 22, wherein said loading step (a) comprises contacting said adsorbent with a physiological saline solution of potassium hexachloroosmate(IV).

* * * * *